(12) United States Patent
Kim et al.

(10) Patent No.: US 10,188,770 B2
(45) Date of Patent: Jan. 29, 2019

(54) DENTAL IMPLANT HAVING ENHANCED EARLY STABILITY AND METHOD FOR MANUFACTURING SAME

(71) Applicant: OSSTEMIMPLANT CO., LTD., Seoul (KR)

(72) Inventors: Su Kyoung Kim, Busan (KR); Eun Jung Kang, Busan (KR); Ju Dong Song, Busan (KR); Tae Gwan Eom, Busan (KR); Kyoo Ok Choi, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 13 days.

(21) Appl. No.: 15/817,569

(22) Filed: Nov. 20, 2017

(65) Prior Publication Data

US 2018/0071435 A1 Mar. 15, 2018

Related U.S. Application Data

(63) Continuation-in-part of application No. 14/369,177, filed on Jun. 26, 2014, now abandoned.

(51) Int. Cl.
*A61C 8/00* (2006.01)
*A61L 27/54* (2006.01)
(Continued)

(52) U.S. Cl.
CPC ............ *A61L 27/54* (2013.01); *A61C 8/0006* (2013.01); *A61C 8/0013* (2013.01); *A61K 38/1875* (2013.01); *A61L 27/50* (2013.01); *A61C 2008/0046* (2013.01); *A61K 31/66* (2013.01); *A61K 31/675* (2013.01); *A61L 2300/216* (2013.01); *A61L 2300/40* (2013.01); *A61L 2300/414* (2013.01); *A61L 2400/18* (2013.01);
(Continued)

(58) Field of Classification Search
CPC ....... A61C 8/0006; A61C 8/0013; A61C 8/00; A61C 8/0015; A61L 27/54; A61L 2300/40; A61L 2430/02; A61L 2430/12; A61K 38/1875; A61K 31/66; A61K 31/675
USPC ............. 433/172, 173, 174, 175, 176, 201.1
See application file for complete search history.

(56) References Cited

U.S. PATENT DOCUMENTS 6,214,049 B1 * 4/2001 Gayer ................. A61C 8/0006
623/16.11
6,461,385 B1 * 10/2002 Gayer ................. A61C 8/0006
623/23.51
(Continued)

FOREIGN PATENT DOCUMENTS

JP 2010-162363 A 7/2010
JP 2011-527205 A 10/2011
(Continued)

OTHER PUBLICATIONS

International Search Report for International Application No. PCT/KR2012/008000.

*Primary Examiner* — Nicholas Lucchesi
(74) *Attorney, Agent, or Firm* — LRK Patent Law Firm

(57) ABSTRACT

A dental implant and a method for manufacturing same which assure early stability and fixation power of an implant by suppressing early osteolysis after an implant procedure, and allowing better bone coherence of the implant surface during an osteogenic period by controlling the speed of bone remodeling.

2 Claims, 7 Drawing Sheets

(51) Int. Cl.
*A61C 8/02* (2006.01)
*A61K 38/18* (2006.01)
*A61L 27/50* (2006.01)
*A61K 31/66* (2006.01)
*A61K 31/675* (2006.01)

(52) U.S. Cl.
CPC ....... *A61L 2430/02* (2013.01); *A61L 2430/12* (2013.01)

(56) References Cited

U.S. PATENT DOCUMENTS

| | | | | |
|---|---|---|---|---|
| 7,909,605 | B2* | 3/2011 | Ihde | A61C 8/001 433/174 |
| 8,303,976 | B2* | 11/2012 | Sapieszko | A61F 2/28 424/422 |
| 8,475,824 | B2* | 7/2013 | McKay | A61L 27/446 424/423 |
| 8,492,335 | B2* | 7/2013 | Kestler | A61K 38/1858 514/8.2 |
| 8,940,320 | B2* | 1/2015 | Schlottig | A61C 8/0016 424/435 |
| 9,050,391 | B2* | 6/2015 | Schlottig | A61L 27/32 |
| 2007/0077267 | A1* | 4/2007 | Molz, IV | A61L 27/227 424/423 |
| 2007/0287129 | A1* | 12/2007 | Ihde | A61C 8/001 433/174 |
| 2008/0286328 | A1* | 11/2008 | Schlottig | A61L 27/32 424/423 |
| 2009/0130177 | A1* | 5/2009 | Schlottig | A61C 8/0013 424/435 |
| 2011/0182962 | A1* | 7/2011 | McKay | A61L 27/446 424/423 |
| 2012/0114731 | A1* | 5/2012 | Vikinge | A61L 27/34 424/423 |
| 2012/0195952 | A1* | 8/2012 | King | A61K 31/00 424/426 |
| 2013/0138221 | A1* | 5/2013 | Junker | A61K 31/675 623/23.57 |
| 2014/0356814 | A1* | 12/2014 | Kim | A61L 27/54 433/173 |

FOREIGN PATENT DOCUMENTS

| | | |
|---|---|---|
| KR | 10-2007-0012783 A | 1/2007 |
| KR | 10-0736826 | 7/2007 |
| KR | 10-2008-0111243 A | 12/2008 |
| KR | 10-2009-0117585 A | 11/2009 |
| KR | 10-2009-0117807 A | 11/2009 |
| KR | 10-2010-0017882 A | 2/2010 |
| KR | 10-2010-0057796 B1 | 6/2010 |
| KR | 10-2010-0076867 A | 7/2010 |
| KR | 10-2011-0082658 A | 7/2011 |
| WO | 2011/128424 A1 | 10/2011 |

* cited by examiner

DENTAL IMPLANT HAVING ENHANCED EARLY STABILITY AND METHOD FOR MANUFACTURING SAME

CROSS-REFERENCE TO RELATED APPLICATIONS

This application is a continuation-in-part of U.S. patent application Ser. No. 14/369,177, filed Jun. 26, 2014, which was the National Stage of International Application No. PCT/KR2012/008000, filed Oct. 4, 2012, which claimed priority to Korean Patent Application No. 10-2011-0143049, filed Dec. 27, 2011, the disclosures of which are incorporated in their entireties herein by reference.

BACKGROUND OF THE INVENTION

1. Field of the Invention

The present discloser relates to a dental implant with enhanced initial stability and a method for manufacturing the same and, more particularly, to a dental implant and a method for manufacturing the same, which can ensure initial stability and fixation of the implant by inhibiting early bone resorption after implant procedure and, at the same time, enhance osseointegration at an implant-bone interface during bone growth by controlling the bone remodeling rate.

2. Description of Related Art

Dental implants (hereinafter simply referred to as implants) are artificial teeth, which can be used to permanently replace missing teeth, and are widely used to restore the masticatory function of partially or completely edentulous patients. Therefore, the dental implants should be designed to functionally act as actual teeth and, at the same time, to properly distribute the load applied to the teeth, thus enabling long-term use.

The success rate and long-term prognosis of the implant depend on the stability, i.e., fixation that is most affected by bone mass and bone quality of patients. The stability of the implant is expressed by the sum of primary stability (i.e., mechanical stability) that occurs when the implant is brought into contact with the surrounding bone and secondary stability (i.e., biological stability) that results from the formation of new bone tissue and the occurrence of osseointegration after implantation of the implant. Moreover, due to the nature of the process in which the stability of the implant is obtained, an area where the stability of the implant decreases is inevitably formed, and thus the time for which the implant is particularly vulnerable to external loads is present.

That is, as shown in FIG. 1A, when the implant is implanted in the alveolar bone, bone resorption to form new bone occurs first in the existing bone, which decreases the stability of the implant, and at the same time, new bone is formed around the implant, which in turn increases the stability of the implant due to osseointegration between the implant and the alveolar bone.

The area where the stability of the implant decreases varies depending on the implant design or surface treatment, but is a common phenomenon that occurs in all dental implants, and the initial stability of the implant is most affected at this time.

Therefore, when the initial stability, which is important for successful osseointegration, is difficult to ensure due to low bone mass and poor bone quality of patients, it may cause early failure of the implant. Moreover, when an excessive load is applied to the implant with low initial stability, the osseointegration may be delayed due to minute vibrations, and thus delayed implantation, in which the load is applied after 3 to 6 months for bone growth, is used in conventional dental implants. That is, according to the conventional implant surface treatment technology, early loading of the implant increases the failure rate of the implant, and when the delayed implantation is performed to prevent this, the implant procedure is extended, which is very problematic.

In order to solve the above problems and enhance the mechanical stability between the implant and the bone, various attempts have been made to ensure the initial stability of the implant by changing the length or diameter of the implant or by introducing a special design for facilitating self-tapping. Moreover, in order to enhance the biological stability between the implant and the bone by osteogenesis, various methods have been attempted to enhance the initial stability of the implant by applying bone growth factors, extracellular matrix molecules, polymer carriers, etc. to the implant.

As such, various methods have been attempted to ensure the initial stability of the implant, but a plan to ensure the initial stability after implantation of the implant has not been developed so far, which makes it difficult to enable early loading and reduce treatment period.

SUMMARY OF THE INVENTION

Accordingly, the present discloser has been made to solve the above-described problems, and an object of the present discloser is to a dental implant and a method for manufacturing the same, which can ensure initial stability after implantation of the implant and enhance osseointegration at an implant-bone interface during bone growth, thus enabling early loading and reducing treatment period.

Moreover, the present discloser also provides dental implant, which has a significantly enhanced osseointegration at the implant-bone interface for a long period of time such as three years.

To achieve the above objects, the present discloser provides a dental implant comprising a roughened surface and an osteoclast activity inhibitor coating film which is formed on the surface of the dental implant to enhance initial stability of the implant and osseointegration at an implant-bone interface.

Moreover, the present discloser provides a method for manufacturing a dental implant, the method comprising the steps of: roughening a surface of a dental implant; subjecting the roughened surface of the dental implant to hydrophilization treatment; and forming an osteoclast activity inhibitor coating film on the surface of the hydrophilized surface of the dental implant.

Meanwhile, the osteoclast activity inhibitor for application to alveolar bone can be applied to the surface of the alveolar bone, which is in contact with a dental implant, before implantation of the implant to inhibit bone resorption of the alveolar bone, thus enhancing initial stability of the implant and osseointegration at an implant-bone interface.

The osteoclast activity inhibitor is used to inhibit early bone resorption of the alveolar bone and may comprise alendronate, zolendronate, or pharmaceutically acceptable salts, esters, and acids thereof.

Furthermore, the osteoclast activity inhibitor coating film may further comprise a bone growth factor such as rhBMP-2 to promote osseointegration of the implant. In addition, the hydrophilization treatment may be performed by plasma or ultraviolet treatment on the surface of the dental implant.

Advantageous Effects

According to the present discloser, it is possible to ensure initial stability and fixation of the implant after implantation by coating the surface of the dental implant with an osteoclast activity inhibitor that inhibits the activity of osteoclasts and, at the same time, enhance osseointegration at an implant-bone interface during bone growth by controlling the bone remodeling rate, thus enabling early loading after implant procedure and reducing treatment period.

Moreover, the present discloser may provide dental implant, which has a significantly enhanced osseointegration at the implant-bone interface for a long period of time such as three years.

DETAILED DESCRIPTION OF THE INVENTION

The present discloser provides a dental implant comprising a roughened surface and an osteoclast activity inhibitor coating film which is formed on the surface of the dental implant to enhance initial stability of the implant and osseointegration at an implant-bone interface.

Moreover, the present discloser provides a method for manufacturing a dental implant, the method comprising the steps of: roughening a surface of a dental implant; subjecting the roughened surface of the dental implant to hydrophilization treatment; and forming an osteoclast activity inhibitor coating film on the surface of the hydrophilized surface of the dental implant.

Meanwhile, the osteoclast activity inhibitor for application to alveolar bone can be applied to the surface of the alveolar bone, which is in contact with a dental implant, before implantation of the implant to inhibit bone resorption of the alveolar bone, thus enhancing initial stability of the implant and osseointegration at an implant-bone interface.

The dental implant and the method for manufacturing the same in accordance with aspects of the present discloser will be described in detail with reference to the accompanying drawings.

First, as used herein, the term "implant" refers to a substitute for restoring lost body tissue, and the term "dental implant" refers to a substitute intended to restore the original function of a tooth in a manner that a fixture is embedded and integrated in the alveolar bone, from which a natural dental root is removed, to replace the root of a missing tooth and then an artificial tooth is fixed onto the top of the fixture.

In particular, in the present discloser, the surface of the dental implant refers to the surface of the fixture that can be integrated in the alveolar bone and may be made of titanium or a titanium alloy comprising titanium and at least one of aluminum, tantalum, niobium, vanadium, zirconium, platinum, magnesium, and sodium.

Figure 1A:
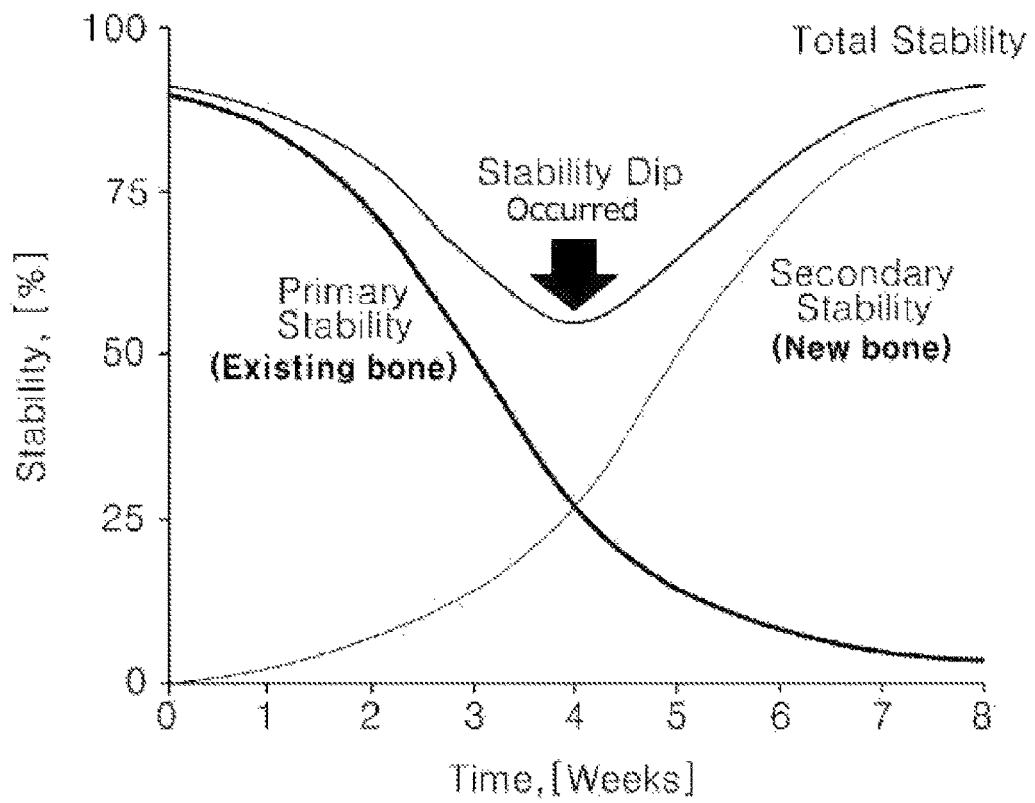
FIG. 1A is a diagram showing the principle of decreased initial stability after implant procedure.

As shown in FIG. 1A, when the implant is implanted in the alveolar bone, bone resorption to form new bone occurs first in the existing bone, which decreases the stability of the implant, and at the same time, new bone is formed around the implant, which in turn increases the stability of the implant due to osseointegration between the implant and the alveolar bone. Due to the nature of the process in which the stability of the implant is obtained, an area where the stability of the entire implant decreases is inevitably formed, and thus the time for which the implant is particularly vulnerable to external loads is present. Therefore, when an excessive load is applied to the implant with low initial stability, the osseointegration may be delayed due to minute vibrations.

Figure 1B:
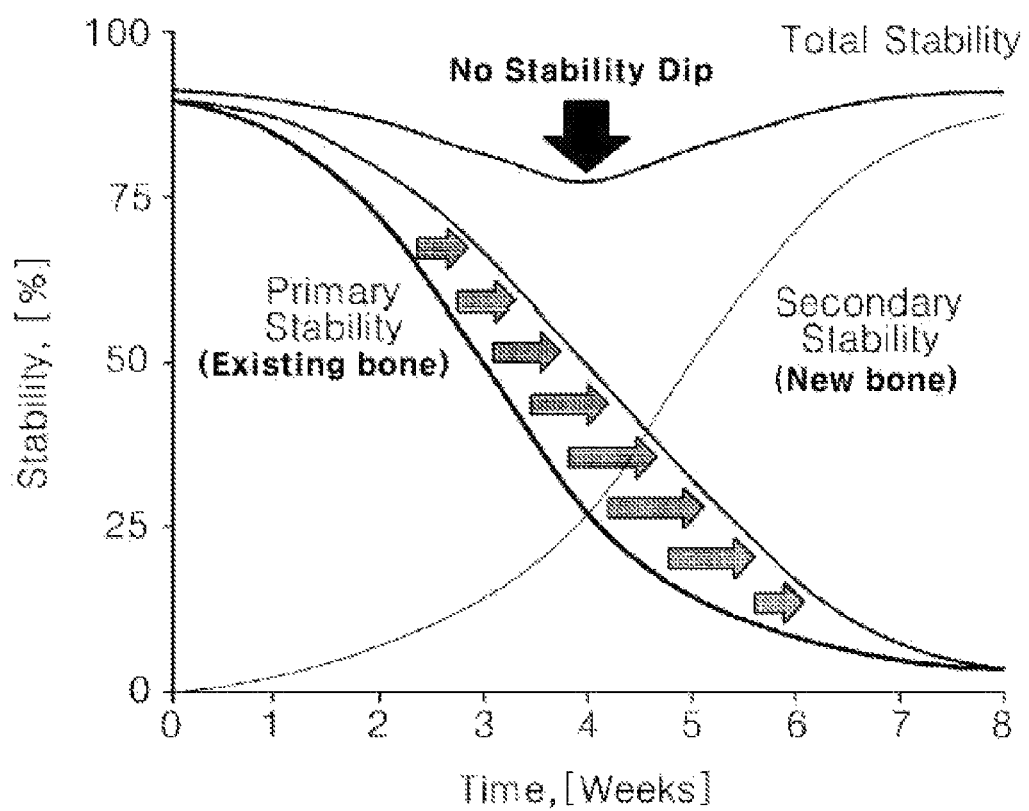
FIG. 1B is a diagram showing the principle of increased initial stability after implant procedure according to the present discloser.

In the present discloser, in order to solve these problems, the osteoclast activity inhibitor coating film, which can inhibit early bone resorption of the alveolar bone, is formed on the implant surface. When the implant is coated with the osteoclast activity inhibitor and then implanted in the alveolar bone, the osteoclast activity inhibitor coated on the implant surface is released from the alveolar bone to the surrounding bone. The released osteoclast activity inhibitor is adsorbed onto the surrounding bone to inhibit the activity of osteoclasts, which delays bone remodeling at an implant-bone interface fixed to the alveolar bone to alleviate the decrease in primary stability of the implant, thus increasing the initial stability of the implant as shown in FIG. 1B. Moreover, the implant coated with the osteoclast activity inhibitor of the present discloser maintains the increase in the initial stability due to an increased osseointegration period, thus enhancing the osseointegration at the implant-bone interface.

That is, the implantation of the implant coated with the osteoclast activity inhibitor according to the present discloser can ensure the initial stability and fixation of the implant by minimizing the area where the stability of the implant decreases and, at the same time, enable early loading of the implant, thus preventing delay in osseointegration due to minute vibrations and reducing the osseointegration period.

Figure 2:
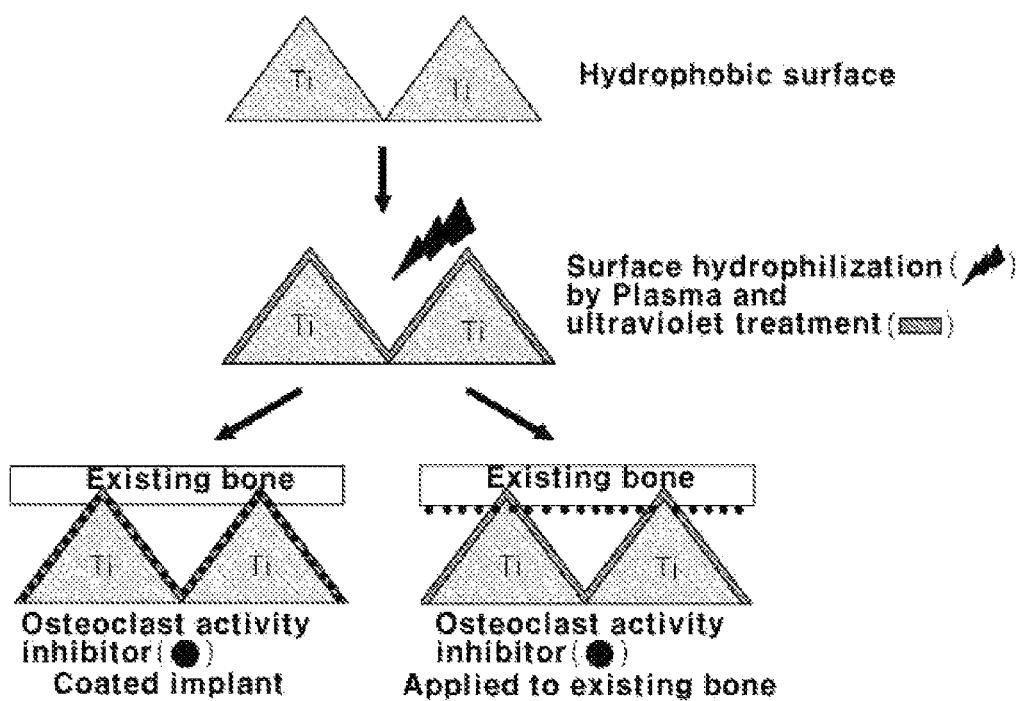
FIG. 2 is a flowchart showing the preparation and implantation of an implant coated with an osteoclast activity inhibitor in accordance with an embodiment of the present discloser.

Moreover, as shown in FIG. 2, the osteoclast activity inhibitor may not be coated directly on the implant, but may be applied directly to the surface of the alveolar bone, which is in contact with the implant, before implantation of the implant, thus obtaining the same effect. Moreover, the osteoclast activity inhibitor may be applied in the form of a solution or in a dried state to the implant surface or the alveolar bone surface to facilitate its release and absorption.

The osteoclast activity inhibitor may comprise alendronate, zolendronate, and pharmaceutically acceptable salts, esters, and acids thereof.

Furthermore, the osteoclast activity inhibitor coating film may further comprise a bone growth factor such as (rh) BMP-2 to promote osseointegration of the implant.

Meanwhile, before the step of coating the osteoclast activity inhibitor on the implant surface, the implant surface may be further subjected to the step of roughening the surface and the step of hydrophilization treatment so as to further enhance the osseointegration. The roughening may be performed by various methods such as blasting, resorbable blasting media, acid etching, alkali etching, titanium plasma spray, sandblasting with large grit and acid treatment, anodizing, laser surface processing, etc., and the roughened implant surface has an increased surface area, which enhances the osseointegration of the implant.

Moreover, the hydrophilization treatment of the implant surface may be performed by various methods that can remove organic contaminants from the surface, and as an example, plasma treatment such as RFGD, $O_2$, and room temperature plasma or ultraviolet treatment may be used.

Next, the effect of the present discloser will be described in detail with reference to the following Examples. However, the following Examples are merely illustrative of one or more detailed examples, and the scope of the present discloser is not limited to the following Examples.

Example 1: Preparation of Dental Implant Subjected to Hydrophilization Treatment and Coated with Osteoclast Activity Inhibitor Machined titanium implants were blasted with $Al_2O_3$ powder with a particle size of 1 mm or less at a blast pressure of 1 to 10 atm for 1 to 60 seconds. Macro- & micro-morphology was given to the implant surface by acid treatment using a mixed acid solution, and then the acid-etched dental titanium implant was washed with ethanol for 30 minutes and with distilled water by ultrasonication for 30 minutes and then dried.

In order to impart hydrophilicity to the implants which were subjected to the above processes, the titanium surface was hydrophilized by plasma treatment (RFGD, $O_2$, etc.) for 1 minutes and light radiation (ultraviolet rays, ultraviolet-ozone, etc.) for 5 minutes. Then, a 10 ml solution of 40 μg Alendronate, 40 μg Zolendronate, 1 μg BMP-2, and 40 μg Alendronate+1 μg BMP-2 was uniformly applied to the surface, and the prepared implants, in which the solution was not dried, were used in the following Examples 2, 3 and 4.

Example 2: Animal Experiments for Measurement of Implant Stability Quotients to Evaluate Initial Stability of Dental Implants Coated with Osteoclast Activity Inhibitor In order to determine implant stability quotients (ISQs), the dental implants coated with alendronate prepared in Example 1 were implanted in the mandible and tibia of micropigs, and then the resonance frequency analysis (RFA) values were measured for ISQs using Osstell™ Mentor (Integration Diagnostics Ltd., Goteborg, Sweden) and Smartpeg™ (Integration Diagnostics Ltd., Goteborg, Sweden) at 0, 0.5, 1, 1.5, 2, 4, and 6 weeks, respectively. At this time, implants that were not coated with the osteoclast activity inhibitor were used as the negative control group, and implants that were subjected to pre-treatment for hydrophilizing the titanium surface and coated with alendronate were used as the experimental group.

Figure 3:
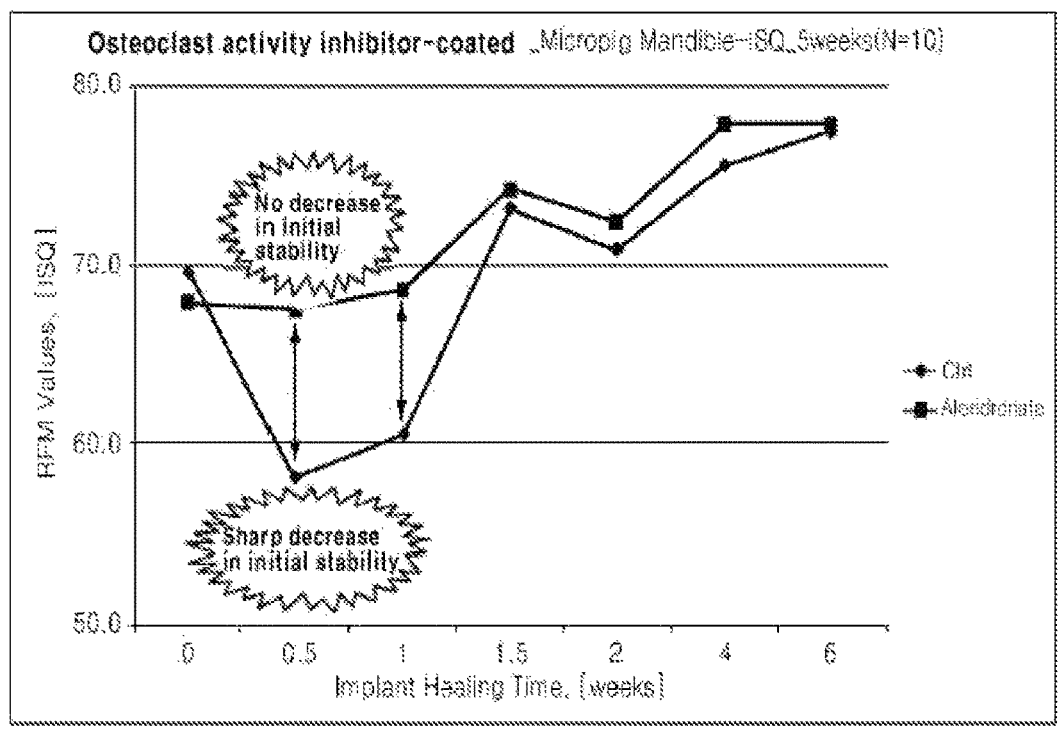
FIGS. 3 and 4 show the results of evaluation of initial stability for 6 weeks after implantation of implants, coated with an osteoclast activity inhibitor in accordance with an embodiment of the present discloser, in the mandible and tibia of micropigs.
Figure 4:
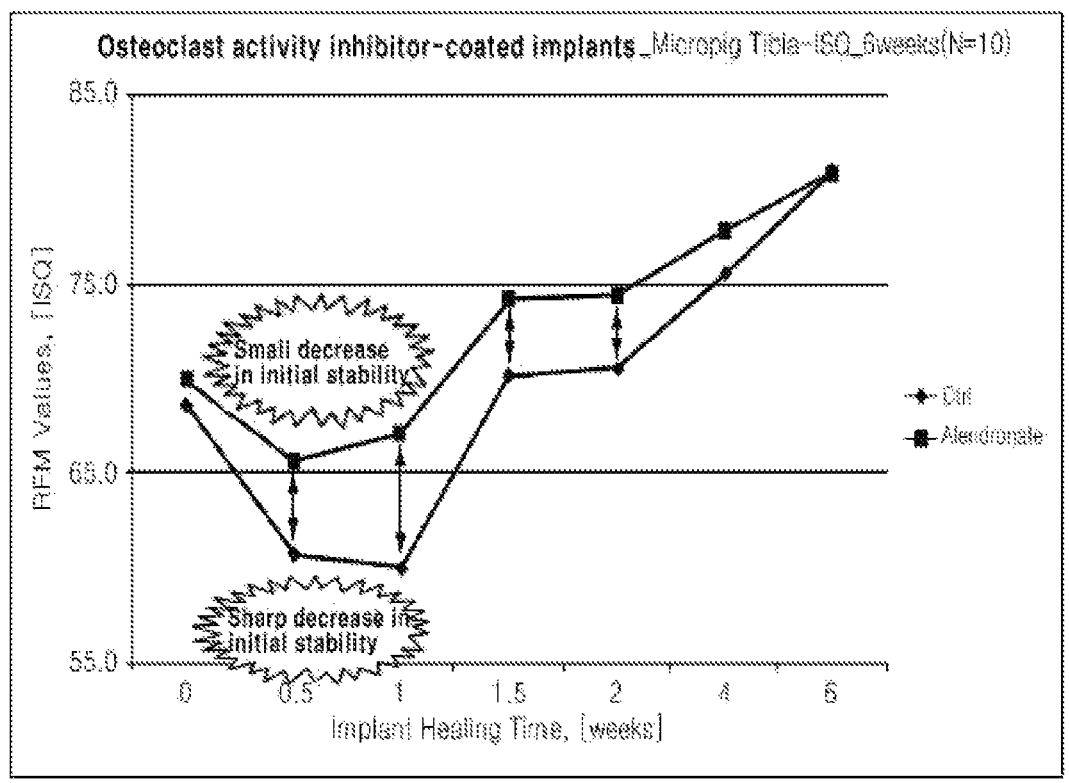

As can be seen from FIGS. 3 and 4, there was little decrease in ISQ values or the degree of the decrease was very lower in the experimental group than in the negative control group, from which it was confirmed that the initial stability of the implant increased.

Example 3: Animal Experiments for Measurement of Osseointegration at Implant-Bone Interface to Evaluate Initial Stability of Dental Implants Coated with Osteoclast Activity Inhibitor In order to determine the osseointegration at the implant-bone interface, the dental implants coated with alendronate and zolendronate prepared in Example 1 were implanted in the tibia of micropigs, and then the removal torques were measured after 16 days for bone growth. At this time, implants that were not coated with the osteoclast activity inhibitor were used as the negative control group, and implants that were subjected to pre-treatment for hydrophilizing the titanium surface and coated with alendronate and zolendronate were used as the experimental group.

Figure 5:
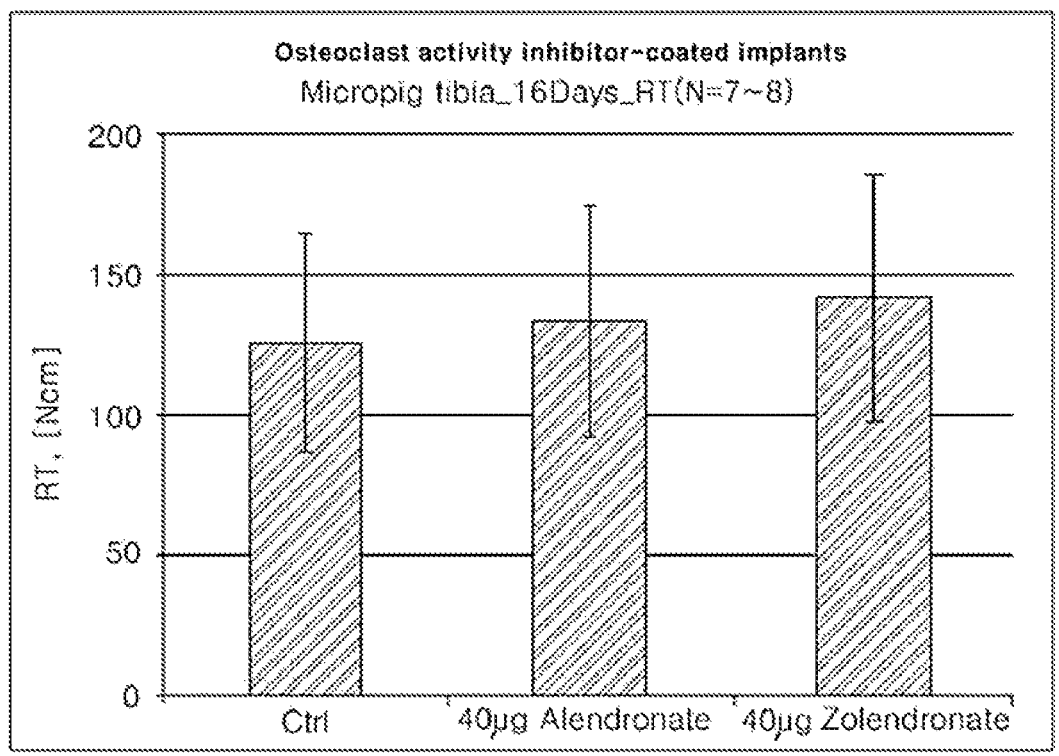
FIG. 5 shows the measurement results of removal torque after 16 days for bone growth after implantation of implants, coated with an osteoclast activity inhibitor in accordance with an embodiment of the present discloser, in the tibia of micropigs.

As shown in FIG. 5, the removal torque was increased by about 6 to 13% in the experimental group compared to the negative control group, from which it was confirmed that the osseointegration at the implant-bone interface increased in the implants coated with the osteoclast activity inhibitor.

Example 4: Animal Experiments for Measurement of Osseointegration at Implant-Bone Interface to Evaluate Initial Stability of Dental Implants Coated with Osteogenic Protein and Osteoclast Activity Inhibitor In order to determine the osseointegration at the implant-bone interface, the dental implants coated with rhBMP-2 and alendronate prepared in Example 1 were implanted in the tibia of micropigs, and then the removal torques were measured after 16 days for bone growth. At this time, implants that were coated only with rhBMP-2, an osteogenic protein, were used as the negative control group, and implants that were subjected to pre-treatment for hydrophilizing the titanium surface and coated with rhBMP-2 and alendronate were used as the experimental group.

Figure 6:
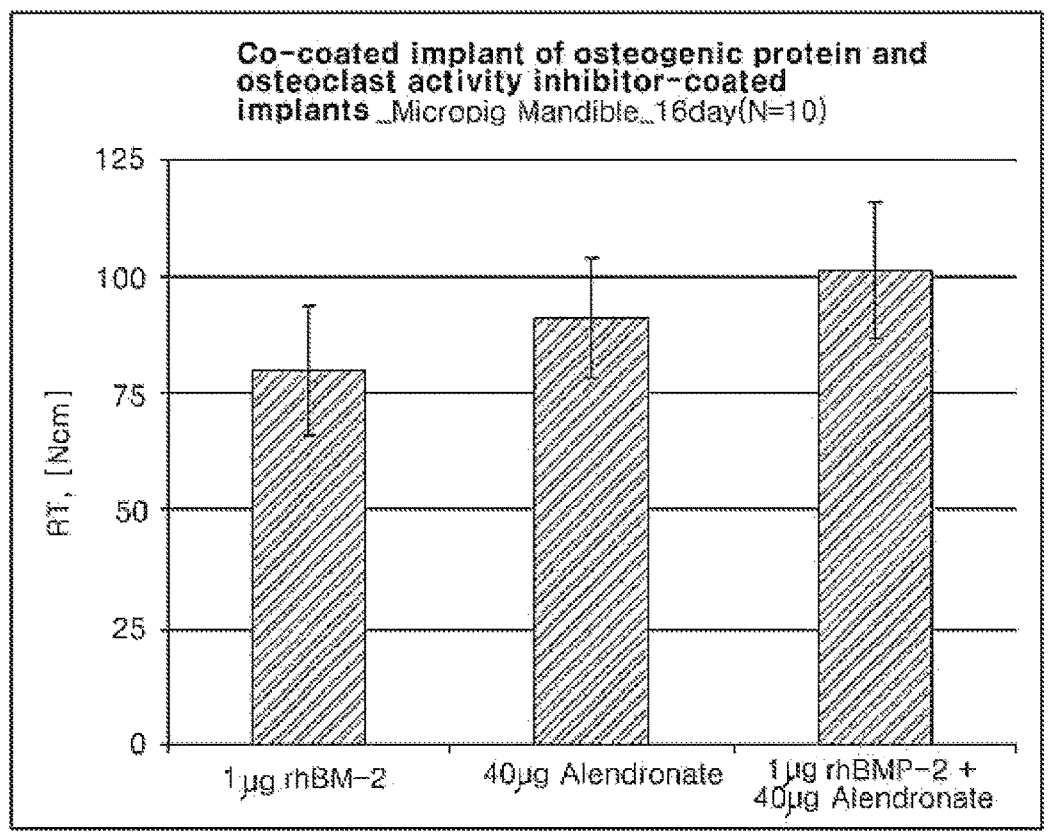
FIG. 6 shows the measurement results of removal torque after 16 days for bone growth after implantation of implants, coated with an osteoclast activity inhibitor and a bone growth factor in accordance with an embodiment of the present discloser, in the tibia of micropigs.

As shown in FIG. 6, the removal torque was increased by about 23% in the experimental group compared to the negative control group, from which it was confirmed that the osseointegration at the implant-bone interface was increased by the use of the osteoclast activity inhibitor in combination with the osteogenic protein.

Example 5: Measurement of Osseointegration at Implant-Bone Interface for Long-Time Storage In order to confirm the long-time storage stabilities of implant, osseointegration at implant-bone interface were measured via removal torque.

Each dental implant was coated with various bisphosphonates as described example 1 and its removal torque was measured just after coating step and 3-year self-storage, respectively.

TABLE 1

Removal torque measurement results for coated implant with various bisphosphonates

| Storage | Bare implant | Implants coated with 10 ml solution of 40 μg bisphosphonate | | | | |
|---|---|---|---|---|---|---|
| Period | Ctrl | Alendronate | Zolendronate | Resendronate | Pamindronate | Ibandronate |
| 0 year | 82.4 ± 10.2 | 100.2 ± 8.4 | 104.4 ± 11.1 | 103.5 ± 9.3 | 99.6 ± 7.9 | 98.4 ± 12.1 |
| 3 year | 81.8 ± 8.6 | 99.4 ± 11.8 | 103.8 ± 8.9 | 83.2 ± 9.3 | 84.1 ± 11.4 | 85.4 ± 12.5 |

According to the results of table 1, implants coated with alendronate or zolendronate showed higher removal torque than other bisphosphonates and bare one (control).

Similarly, osseointegration at implant-bone interface were measured via removal torque for dental implants wherein the osteoclast activity inhibitor coating film further comprises a bone growth factor (BMP-2) as shown in Table 2.

TABLE 2

Removal torque measurement results for coated implant with various bisphosphonates and bone growth factor

| Storage | Bare implant | 1 μg | Implants coated with 10 ml solution of 40 μg bisphosphonate and 1 μg rhBMP-2 | | | | |
|---|---|---|---|---|---|---|---|
| Period | Ctrl | rhBMP-2 | Alendronate | Zolendronate | Resendronate | Pamindronate | Ibandronate |
| 0 year | 79.4 ± 10.5 | 108.2 ± 10.6 | 130.1 ± 9.7 | 134.4 ± 11.9 | 128.1 ± 11.6 | 127.5 ± 12.2 | 128.8 ± 13.4 |
| 3 year | 80.3 ± 12.9 | 104.9 ± 11.4 | 129.8 ± 13.1 | 132.5 ± 10.7 | 108.1 ± 11.6 | 109.7 ± 12.2 | 110.8 ± 13.4 |

As shown in Table 2, the implants coated with both rhBMP-2 and alendronate or zolendronate, showed higher removal torque value than other dental implants.

The present discloser is not limited to the above-described specific embodiments and description, and it will be appreciated by those skilled in the art that changes may be made in these embodiments without departing from the principles and spirit of the discloser, the scope of which is defined in the appended claims and their equivalents.

What is claimed is:

1. A dental implant comprising:
a hydrophilized roughened surface formed by plasma or ultraviolet treatment; and
an osteoclast activity inhibitor coating film which is formed on the hydrophilized roughened surface of the dental implant to enhance initial stability of the implant and osseointegration at an implant-bone interface,
wherein the osteoclast activity inhibitor comprises at least one selected from the group consisting of alendronate, zolendronate, and pharmaceutically acceptable salts, esters, and acids thereof, and
wherein the osteoclast activity inhibitor coating film further comprises a bone growth factor.

2. A method for manufacturing a dental implant, the method comprising the steps of:
roughening a surface of a dental implant to thereby form a roughened surface of the dental implant;
subjecting the roughened surface of the dental implant to hydrophilization treatment performed by plasma or ultraviolet treatment to thereby form a hydrophilized roughened surface of the dental implant; and
forming an osteoclast activity inhibitor coating film on the hydrophilized roughened surface of the dental implant,
wherein the osteoclast activity inhibitor comprises at least one selected from the group consisting of alendronate, zolendronate, and pharmaceutically acceptable salts, esters, and acids thereof, and
wherein the osteoclast activity inhibitor coating film further comprises a bone growth factor.

* * * * *